United States Patent [19]

Arnold et al.

[11] Patent Number: 4,873,058

[45] Date of Patent: Oct. 10, 1989

[54] FLOW DIVIDER FOR GAS CHROMATOGRAPHS

[75] Inventors: Kraft-Ulrich Arnold, Karlsruhe, Fed. Rep. of Germany; Fernand Clauss, Beinheim, France

[73] Assignee: Siemens Aktiengesellschaft, Berlin and Munich, Fed. Rep. of Germany

[21] Appl. No.: 162,538

[22] Filed: Mar. 1, 1988

[30] Foreign Application Priority Data

Mar. 16, 1987 [DE] Fed. Rep. of Germany ....... 3708504

[51] Int. Cl.$^4$ ............................................ G01N 30/02
[52] U.S. Cl. ....................................... 422/89; 55/197; 73/23.1
[58] Field of Search .......................... 422/89; 73/23.1; 55/197

[56] References Cited

U.S. PATENT DOCUMENTS 3,513,636  5/1970  Halasz ................................... 55/197
4,035,168  7/1977  Jennings ................................. 55/67

OTHER PUBLICATIONS

McNair, Dr. Harold M., "Recent Advances in GC", Apr. 1985, p. 7.
Dodo et al., "Optimized Flow Programming for Temperature-Programmed Gas Chromatography", J. of Chromatography, 328 (1985), pp. 49–53.
Lee et al., Open Tubular Column Gas Chromatography, Theory and Practice, ISBN 0-471-88024-8 (1984), pp. 195–198 and 227.
Nestrick et al, "Low Splitting-Ratio Injector for Gas Chromatography Analytical Chemistry", vol. 55, No. 12, Oct. 1983, 2009–2011.
Wicar, S., "Mass Flow Control and Temperature Programming in Gas Chromatography", J. of Chromatography, 295 (1984), pp. 395–403.
Lee et al., "Open Tubular Column Gas Chromatography, Theory and Practice", ISBN 0-471-88024 (1984), pp. 116–118 and 166.
J & W Scientific, "High Resolution Chromatography Products", 1987/1988, pp. 118–119.
Jennings et al., "Sample Injection in Gas Chromatography", J. of Chromatographic Science, vol. 24, Jan. 1986, pp. 34–40.
SGE, "Column Pressure Switching System", Mar. 1984.
Wright, "A Multidimensional Conversion System for Capillary GC", American Laboratory, Aug. 1985.

Primary Examiner—Robert J. Hill, Jr.
Assistant Examiner—Marcello Iris Fruchter
Attorney, Agent, or Firm—Mark H. Jay

[57] ABSTRACT

Upstream and downstream flow dividers are connected in series between a sample dispenser and a gas chromatograph separation column. The downstream flow divider is connected to a source of carrier gas, and the system can be backflushed with carrier gas to remove residual quantities of sample material and elute the sample.

1 Claim, 1 Drawing Sheet

FLOW DIVIDER FOR GAS CHROMATOGRAPHS

BACKROUND OF THE INVENTION

The invention relates to gas chromatography, and more particularly relates to flow dividers for gas chromatographs.

To analyze liquids or gases using gas chromatography, a sample is metered or evaporated and transported into the separation column using a stream of carrier gas. It is prohibitively expensive to produce a gas chromatograph which will accept less than 0.5 μL of sample fluid into the sample evaporator, but conventional capillary separation columns can only achieve good separation using quantities which are two decimal orders of magnitude less. As a result, a flow divider or "split" is connected between the metering/evaporating device and the chromatograph separation column. The flow divider divides the mixture of carrier gas and sample using a ratio which is set by the operator to prevent the quantity of sample in the chromatographic column from becoming excessive.

Such a flow divider or split utilizes a split chamber which has a port to the atmosphere, a connection to the sample dispenser and a connection to the separation column. The devision ratio of the flow divider is determined by the flow resistances of the separation column and a choke which is mounted on the port.

Samples of polar materials and samples having high boiling points can be adsorbed on the walls of the split chamber. Consequently, subsequent runs can become contaminated by "tailing", in which small quantities of residual sample material are released into the stream of carrier gas which is directed into the column during subsequent analyses.

It would be advantageous to provide a flow divider for gas chromatographs which reduced the effect of wall adsorption and consequential "tailing" contamination.

SUMMARY OF THE INVENTION

In accordance with the invention, two flow dividers are connected in series with each other between a sample dispenser and a separation column. A valve connects the split chamber of the downstream flow divider with a source of carrier gas, and another valve connects the source of carrier gas with the sample dispenser.

The overall division ratio of the system is determined by the division ratios of each of the dividers. Once the sample has entered the column, the system can be backflushed by directing carrier gas into the downstream flow divider and shutting off the flow of carrier gas to the sample dispenser. This removes sample components which have been adsorbed in the split chamber walls of the flow dividers.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
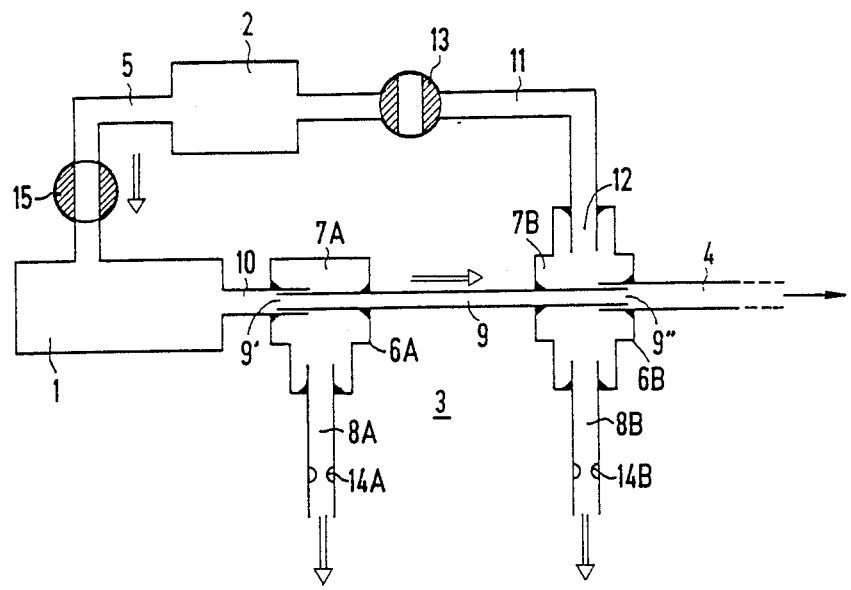
FIG. 1 schematically illustrates a preferred embodiment of the invention during analysis of a sample.

In all of the Figures, the same element is always indicated by the same reference numeral.

A sample dispenser 1 receives liquid or gas samples, in volumes which are on the order of microliters. The sample dispenser 1 may be a metering device, an evaporating device or both. It introduces the evaporated or metered sample into a stream of carrier gas which is drawn from source 2 and introduced into the sample dispenser 1 through an open valve 15 in conduit 5.

Referring first to FIG. 1, the sample (not shown), entrained in a stream of carrier gas (not shown), is then directed into a flow divider system 3 through a line 10. The system 3 has two flow dividers 6A and 6B which are connected in series with each other between the sample dispenser 1 and the separation column 4. The flow divider 6A is upstream, i.e. closer to the sample dispenser 1, and the downstream flow divider 6B is connected to the separation column 4. The flow dividers 6A and 6B are connected together through a transfer line 9, which is connected to the upstream flow divider 6A at end 9' and to downstream flow divider 6B at end 9". The end 9' extends into the open end of line 10, and the end 9" extends into the column 4.

Each of the flow dividers 6A and 6B has a split chamber (7A and 7B respectively) which is ported to the atmosphere via ports 8A and 8B respectively. Port 8A is fitted with a choke 14A and port 8B is fitted with a choke 14B. The overall division ratio of the flow divider system 3 is determined by the flow resistance of the column 4 as compared to the flow resistances of the chokes 14A and 14B.

Figure 2:
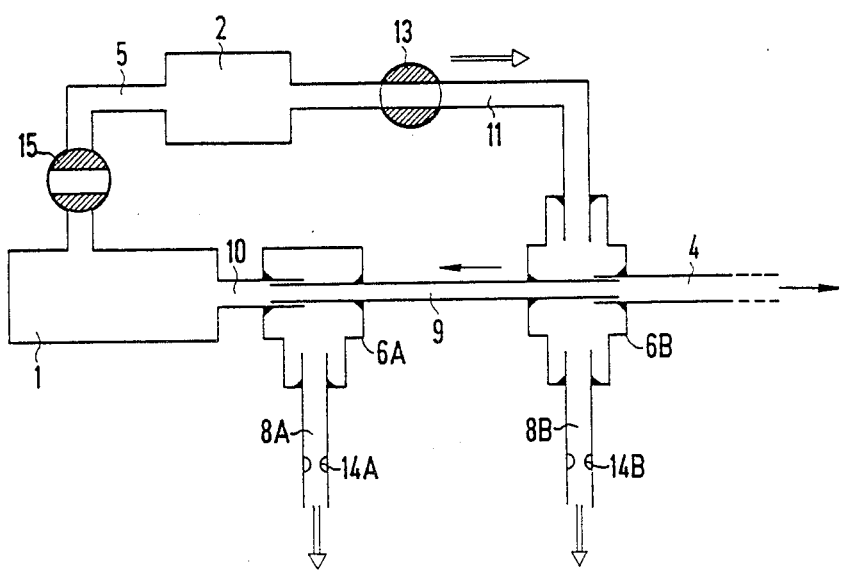
FIG. 2 is a schematic diagram of the preferred embodiment of the invention during backflushing, after the sample has entered the column.

The source 2 is connected to the split chamber 7B of the downstream flow divider 6B through a valve 13 in a line 11. During the sampling process, this valve 13 is closed. The analysis process then proceeds with the evaporated/metered sample from the sample dispenser 1 being divided by the two flow dividers 6A and 6B and directed to the separation column 4. However, after the sample has been transferred to the column 4, the valve 13 is opened and the valve 15 is closed. FIG. 2 illustrates this situation. This backflushes the two flow dividers 6A and 6B and all residues of the sample are flushed out the ports 8A and 8B. Furthermore, the carrier gas enters the downstream flow divider 6B and enters the separation column 4 to elute the sample.

Those skilled in the art will understand that changes can be made in the preferred embodiments here described, and that these embodiments can be used for other purposes. Such changes and uses are within the scope of the invention, which is limited only by the claims which follow.

We claim:

1. A flow divider system for use in gas chromatographs and adapted to be connected to a sample dispenser, a separation column and a source of carrier gas, comprising:
    upstream and downstream flow dividers, each having a split chamber, an inlet, an outlet, and a choked port, the inlet of the upstream flow divider being connected to the sample dispenser, the outlet of the upstream flow divider adapted to be connected to the inlet of the downstream flow divider, and the outlet of the downstream flow divider being connected to the separation column;
    means for connecting and disconnecting the source of carrier gas with the split chamber of the downstream flow divider.

* * * * *